(12) United States Patent
Alarcon et al.

(10) Patent No.: US 11,833,293 B2
(45) Date of Patent: Dec. 5, 2023

(54) DEVICE, METHOD AND SYSTEM FOR LOGGING SMOKING DATA

(71) Applicant: Fontem Holdings 4 B.V., Amsterdam (NL)

(72) Inventors: Ramon Alarcon, Los Gatos, CA (US); Chris Kepner, Campbell, CA (US); Michael Starman, Los Gatos, CA (US); Dennis Christopher Howard, Summerfield, NC (US)

(73) Assignee: Fontem Ventures B.V., Amsterdam (NL)

( * ) Notice: Subject to any disclaimer, the term of this patent is extended or adjusted under 35 U.S.C. 154(b) by 38 days.

(21) Appl. No.: 17/204,685

(22) Filed: Mar. 17, 2021

(65) Prior Publication Data
US 2021/0308392 A1 Oct. 7, 2021

Related U.S. Application Data

(63) Continuation of application No. 14/550,717, filed on Nov. 21, 2014, now Pat. No. 10,973,258.
(Continued)

(51) Int. Cl.
*A24F 47/00* (2020.01)
*A61M 15/06* (2006.01)
(Continued)

(52) U.S. Cl.
CPC ............ *A61M 15/06* (2013.01); *A24F 40/53* (2020.01); *A24F 40/65* (2020.01); *G16H 20/13* (2018.01);
(Continued)

(58) Field of Classification Search
CPC .................................. A24F 40/50; A24F 40/53
See application file for complete search history.

(56) References Cited

U.S. PATENT DOCUMENTS

| 4,771,440 A | 9/1988 | Fromm |
| 6,539,485 B1 | 3/2003 | Liu et al. |
(Continued)

FOREIGN PATENT DOCUMENTS

| CN | 102006790 A | 4/2011 |
| CN | 202172847 U | 3/2012 |
(Continued)

OTHER PUBLICATIONS

Wikipedia, Modulation, Dec. 14, 2012, https://en.wikipedia.org/wiki/Modulation, all pages (Year: 2012).
(Continued)

*Primary Examiner* — Eric Yaary
(74) *Attorney, Agent, or Firm* — Dykema Gossett PLLC

(57) ABSTRACT

A system, a method, a device, and a computer program for detecting, monitoring and logging smoking activity related data. The device can comprise a housing, a power supply located within the housing, an atomizer electrically coupled to the power supply, a liquid solution fluidly coupled to the atomizer, and a data logging device configured to be located within the housing and that can comprise a microcontroller, a memory, and a data interface. The data logging device can be configured to detect, monitor, and log smoking activity data, and a data logging device that can comprise a microcontroller, a memory, and a data interface. The data logging device can be configured to detect, monitor, and log smoking activity data.

19 Claims, 13 Drawing Sheets

Related U.S. Application Data

(60) Provisional application No. 61/907,239, filed on Nov. 21, 2013.

(51) Int. Cl.
*A24F 40/65* (2020.01)
*G16H 20/13* (2018.01)
*G16H 40/63* (2018.01)
*A24F 40/53* (2020.01)
*A24F 40/50* (2020.01)
*G16H 10/60* (2018.01)
*A24F 40/10* (2020.01)
*G01D 9/00* (2006.01)

(52) U.S. Cl.
CPC .............. *G16H 40/63* (2018.01); *A24F 40/10* (2020.01); *A24F 40/50* (2020.01); *G01D 9/005* (2013.01); *G16H 10/60* (2018.01)

(56) References Cited

U.S. PATENT DOCUMENTS

| | | |
|---|---|---|
| 8,851,081 B2 | 10/2014 | Fernando et al. |
| 2002/0038432 A1 | 3/2002 | Hsu |
| 2004/0031497 A1 | 2/2004 | Likness et al. |
| 2004/0153543 A1 | 8/2004 | Thomas |
| 2008/0070614 A1* | 3/2008 | Ogushi .............. H04W 52/0216 455/522 |
| 2009/0320863 A1 | 12/2009 | Fernando et al. |
| 2011/0036346 A1 | 2/2011 | Cohen et al. |
| 2011/0215758 A1 | 9/2011 | Stahlin et al. |
| 2011/0265806 A1 | 11/2011 | Alarcon et al. |
| 2011/0277764 A1 | 11/2011 | Terry et al. |
| 2012/0048266 A1 | 3/2012 | Alelov |
| 2012/0199146 A1 | 8/2012 | Marangos |
| 2013/0042865 A1 | 2/2013 | Monsees et al. |
| 2013/0284192 A1 | 10/2013 | Peleg et al. |
| 2013/0319435 A1 | 12/2013 | Flick |
| 2013/0340775 A1 | 12/2013 | Juster et al. |
| 2014/0069444 A1* | 3/2014 | Cyphert .................. A24F 1/00 131/194 |
| 2014/0091143 A1 | 4/2014 | Sweeney |
| 2014/0107815 A1 | 4/2014 | LaMothe |
| 2014/0174459 A1 | 6/2014 | Burstyn |
| 2014/0278250 A1 | 9/2014 | Smith et al. |
| 2014/0278258 A1 | 9/2014 | Shafer |
| 2014/0301491 A1 | 10/2014 | Yamamoto |
| 2014/0305450 A1 | 10/2014 | Xiang |
| 2015/0001923 A1 | 1/2015 | Haury et al. |
| 2015/0173124 A1 | 6/2015 | Qiu |
| 2015/0224268 A1 | 8/2015 | Henry et al. |
| 2015/0230521 A1 | 8/2015 | Talon |
| 2015/0245660 A1 | 9/2015 | Lord |
| 2016/0219938 A1 | 8/2016 | Mamoun et al. |
| 2016/0242466 A1 | 8/2016 | Lord et al. |
| 2016/0278435 A1 | 9/2016 | Choikroun et al. |
| 2016/0366939 A1 | 12/2016 | Alarcon et al. |
| 2016/0371437 A1 | 12/2016 | Alarcon et al. |
| 2017/0149473 A1 | 5/2017 | Zhao et al. |

FOREIGN PATENT DOCUMENTS

| | | | |
|---|---|---|---|
| CN | 102970885 A | 3/2013 | |
| WO | 2009127401 A1 | 10/2009 | |
| WO | 2011137453 A2 | 11/2011 | |
| WO | WO-2014169412 A1 * | 10/2014 | .............. A24F 15/18 |
| WO | 2014/205456 A2 | 12/2014 | |
| WO | 2014203083 A2 | 12/2014 | |
| WO | 2016023809 A1 | 2/2016 | |

OTHER PUBLICATIONS

EE Times, What is Power Line Communication, 2011, https://www.eetimes.com/document.asp?doc_id=1279014 (Year: 2011).
International written opinion and report for PCT/US2014/066950 dated Apr. 16, 2015.

* cited by examiner

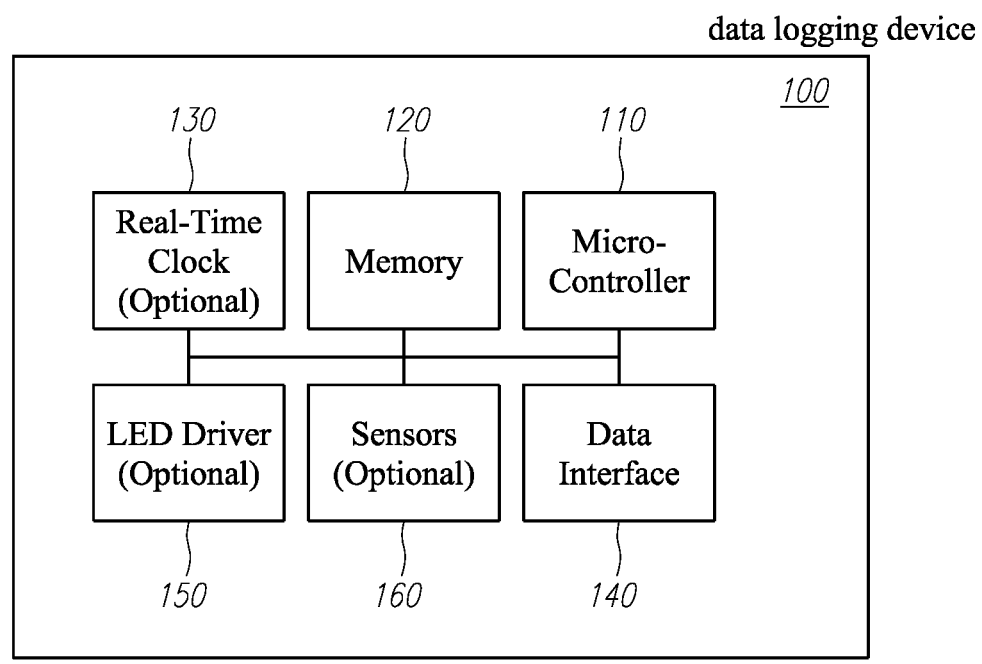
FIG. 1
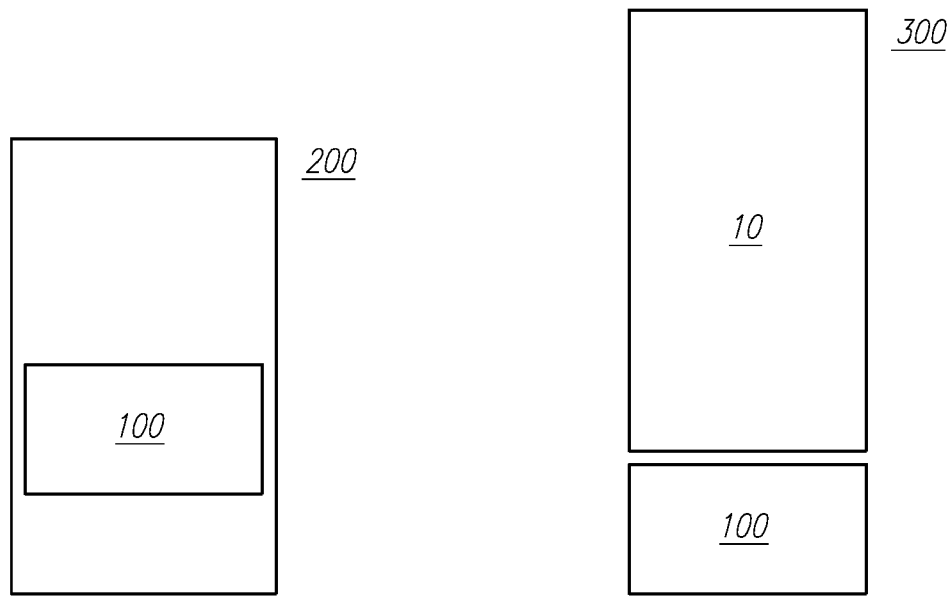
FIG. 2
FIG. 3

DEVICE, METHOD AND SYSTEM FOR LOGGING SMOKING DATA

CROSS REFERENCE TO RELATED APPLICATIONS

This application is a continuation of U.S. application Ser. No. 14/550,717, filed 21 Nov. 2014 (the '717 application), which claims the benefit of U.S. provisional application No. 61/907,239, filed 21 Nov. 2013 (the '239 application). The '717 application, and '239 application are both hereby incorporated by reference as though fully set forth herein.

FIELD OF THE DISCLOSURE

The present disclosure relates to a system, a method, a device, and a computer program for detecting, monitoring, and logging smoking activity related data.

BACKGROUND OF THE DISCLOSURE

Electronic cigarettes, also known as e-cigarettes (eCigs) and personal vaporizers, are electronic inhalers that vaporize or atomize a liquid solution into an aerosol mist that may then be delivered to a user. A typical eCig has a mouthpiece, a battery, a liquid storage area, an atomizer, and a liquid solution. Smokers who try to reduce their smoking or who would like to monitor their smoking habits for any of a variety of reasons, including clinical studies, have to personally monitor and record their smoking habits.

SUMMARY OF THE DISCLOSURE

The present disclosure provides systems, methods, devices, and computer programs for detecting, monitoring, and logging smoking activity data.

According to one non-limiting example of the disclosure, a system, a method, a device, and a computer program are provided for detecting, monitoring, and logging smoking activity data.

In one embodiment of the disclosure, the device can comprise a housing, a power supply located within the housing, an atomizer electrically coupled to the power supply, a liquid solution fluidly coupled to the atomizer, and a data logging device configured to be located within the housing and that can comprise a microcontroller, a memory, and a data interface. The data logging device can be configured to detect, monitor, and log smoking activity data.

In another embodiment of the disclosure, a method for transmitting stored smoking data can comprise broadcasting a data set comprising smoking data stored by a data logging device, waiting a predetermined period of time, rebroadcasting the data set a predetermined number of times, and ending broadcasting of the data set.

In another embodiment of the disclosure, a method for transmitting stored smoking data can comprise broadcasting a data set comprising smoking data stored by a data logging device, waiting a predetermined period of time, rebroadcasting the data set a predetermined number of times, and ending broadcasting of the data set.

Additional features, advantages, and embodiments of the disclosure may be set forth or apparent from consideration of the detailed description and drawings. Moreover, it is to be understood that the foregoing summary of the disclosure and the following detailed description, drawings, and attachment are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and, together with the detailed description, serve to explain the principles of the disclosure. No attempt is made to show structural details of the disclosure in more detail than may be necessary for a fundamental understanding of the disclosure and the various ways in which it may be practiced.

FIG. 1 shows an example of a data logging device constructed according to the principles of the disclosure.

FIG. 2 schematically shows an example of a smart eCig (SCig) constructed according to the principles of the disclosure.

FIG. 3 schematically shows an example of a conventional eCig that is retrofitted with the logging device of FIG. 1 to make an SCig according to the principles of the disclosure.

Figure 4A:
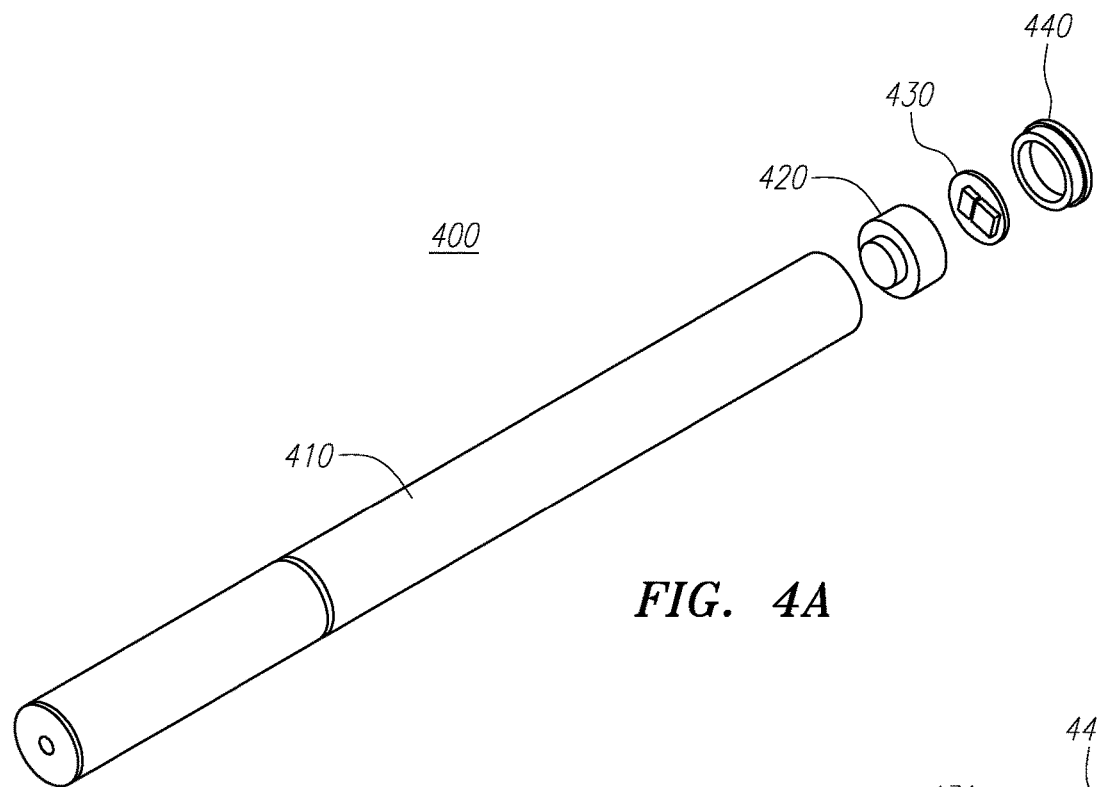
FIG. 4a shows an exploded, isometric view of an example of a conventional eCig that has been retrofitted according to the principles of the disclosure to form an SCig.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following.

FIG. 1 shows an example of a data logging device 100, according to an aspect of the disclosure. The data logging device 100 comprises a microcontroller 110, a memory 120, and a data interface 140. The microcontroller 110 comprises a computer. In one embodiment, the microcontroller 110 can control the data logging function run by the data logging device 100. In another embodiment, the microcontroller 110 can control the data logging function run by the data logging device 100 and can also govern other functions of the SCig. The memory 120 includes a computer-readable medium. The data interface 140 is configured to transmit and/or receive (transceive) logging data signals and control signals from/to the data logging device 100 via a communication link. The data interface 140 may include a power supply line that may be connected to an external power supply. The data interface 140 may be configured to interface with existing circuitry in a conventional eCig (e.g., eCig 10 shown in FIG. 3). In one embodiment the microcontroller 110 can track time, by either having a clock built into the microcontroller 110 or by having a timer that is integral to the microcontroller 110 and can track the amount of time that has passed since a certain point or since a signal or other mechanism was received. In a separate embodiment, the logging device 100 can further comprise a real-time clock 130 to track the amount of time between certain events or to report an internal reference time to a different component of the data logging device 100. The data logging device 100 can also optionally include a light emitting diode (LED) driver 150. The LED driver 150 can send signals to operate an LED (not shown) that can be used as an operational indicator or other visual signal for the end user. The data logging device 100 can optionally also include various sensors 160. The sensors 160 can comprise a resistance measuring circuit, a thermocouple, a thermistor, a photoreceptor, an infrared measuring device, a current sensor, a flow sensor, a pressure sensor, or other similar sensors. These sensors can allow the microcontroller 110 to set or vary the energy delivered to a heating element, the volume of liquid delivered to a heating element in the SCig, or otherwise determine and change various settings within the SCig. The settings can vary, for example, when a slower and lower volume puff is being taken by a user and when a quick and deep puff is being taken by a user.

The data logging device 100 may further include a global positioning satellite (GPS) receiver (not shown), a Bluetooth device, a wireless internet device, and/or a radio frequency identification (RFID) device.

Figure 6:
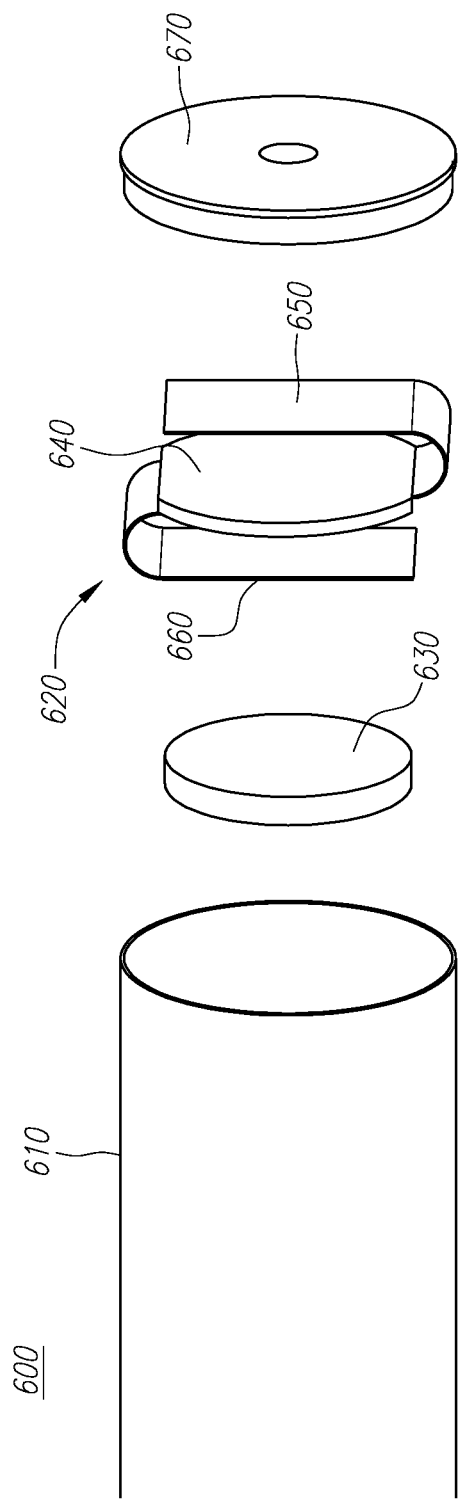
FIG. 6 shows an example of a mouthpiece that may be attached to a traditional tobacco-based cigarette, according to the principles of the disclosure.

A data logging device 100 as discussed in the present disclosure may be a dedicated circuit within an SCig or a retrofitting unit (as seen in FIG. 6), or may be incorporated into circuitry that governs the SCig or the retrofitting unit.

FIG. 2 shows an example of an SCig 200. The SCig 200 comprises the logging device 100 (shown in FIG. 1), a power supply (not shown), a mouthpiece (not shown), a liquid or gel solution (a juice) (not shown), and an atomizer (not shown). The SCig 200 may further comprise a liquid storage area (not shown) and/or a heating element (not shown).

FIG. 3 shows an example of a conventional eCig 10 that is retrofitted with the logging device 100 (shown in FIG. 1) to make an SCig 300, according to principles of the disclosure. The eCig 10 may include a conventional electronic cigarette such as, e.g., a Blu™ Original, a Blu™ Premium, a Blu™ Premium 100, or the like.

Referring to FIGS. 1-3, the microcontroller 110 monitors and stores logging data in the memory 120. The logging data comprises SCig log data relating to the characteristics and conditions of the SCig 200/300, including its components (e.g., heating element, liquid storage area, atomizer, juice, battery, etc.) and user activity log data relating to the use of the SCig 200/300 by a user. On the basis of the logging data, the microcontroller 110 may control the amount and timing of delivery of the aerosol payload to the user, including, e.g., the nicotine payload, flavorant payload, as well as control one or more components in the SCig 200/300, including, e.g., the temperature of the heating element, the duration of operation of the SCig 200/300, the amount of juice aerosolized, the rate of aerosol generation, and the like.

The microcontroller 110 may include artificial intelligence (AI) such as, e.g., fuzzy logic, neural network, adaptive algorithms, or the like, so as to acquire historical user log data and customize operation of the SCig 200/300 to the user. The microcontroller 110 may process the logging data and run a predictive algorithm to predict user behavior to take anticipatory actions with regard to the SCig 200/300, such as, e.g., waking the SCig 200/300 from a sleep mode (or setting to sleep) at a particular time and/or date, activating (or deactivating) the heater element at a particular time/date, operating (or turning off) the heater element for a determined duration, and the like. The microcontroller 110 may also wake the SCig 200/300 from a sleep mode (or set to sleep) based on the logging data, including, e.g., a predetermined date, the manufacturing date, and the like.

SCig log data can comprise data such as, e.g., date of manufacture of the SCig (and/or a component in the SCig), expiration date of the SCig (and/or a component in the SCig), amount of time the SCig has been in use (e.g., hours of operation), power supply voltage, battery type, battery power remaining, number of times battery has been recharged, temperature of heater, heater type, nicotine level delivered, flavor in use, ingredient list, amount of cartomizer left, lot number, cartomizer type, cartomizer identification number, time/date of retrofitting the eCig 10 with the logging device, and the like.

The user activity log data comprises data such as, e.g., time of each use by the user (e.g., puff time), day of the week of each use by the user (e.g. puff day), date of each use by the user (e.g., puff date), duration of each use (e.g., puff duration), geographic location at each use (e.g., puff location), pressure during each use (e.g., puff draw strength or pressure), volume of each use (volume of puff), nicotine level delivered (payload) to user at each use (e.g., nicotine per puff), identification of ingredients in aerosol delivered to user at each use (e.g., ingredient identification), amount of each ingredient in aerosol delivered to user at each use (e.g., ingredient amount), user identification, user age, number of years user has been smoking, average number of cigarettes smoked per day by user, and the like.

FIG. 4a shows an exploded view of an embodiment of an SCig 400 that is constructed according to the principles of the disclosure. The SCig 400 comprises a conventional eCig 410 and a removable/attachable data logging circuitry 430. The SCig 400 may comprise a data logging circuitry board support 420 and/or a cover (e.g., a lens) 440. The cover 440 may be an original part of the conventional eCig 410. The data logging circuitry 430 may include the logging device 100 (shown in FIG. 1).

The conventional eCig 410 may be retrofitted with the data logging circuitry 430 by removing the existing lens cover (e.g., cover 440), if any exists, inserting the data logging circuitry board support 420, inserting the data logging circuitry 430 and replacing (or placing) the cover 440. The data logging circuitry board support 420 may include contact points and/or communication links for conveying the logging data signals and control signals between the conventional eCig 410 and data logging circuitry 430. The control signals may include sensor signals received from one or more sensors provided in the conventional eCig 410, such as, e.g., a pressure sensor (not shown), a temperature sensor (not shown), a voltage sensor (not shown), a capacitive sensor (not shown), or the like. The data logging circuitry board support 420 may include a configuration that is configured to receive the data logging circuitry 430 and hold it snuggly to minimize any forces that may be encountered, such as, e.g., dropping of the SCig 400.

In one embodiment the data logging circuitry board support 420 can already be included within the pre-retrofitted eCig 410. The data logging circuitry board support 420 can comprise a pre-existing circuitry (not shown). The pre-existing circuitry can be used by the eCig 410 to determine when a user is using the eCig 410 and/or to send visual signals to a user. In this embodiment the data logging circuitry board support 420 can be pre-existing circuitry, and the data logging circuitry 430 can be connected to the data logging circuitry board support 420. The data logging circuitry board support 420 can provide control signals to the data logging circuitry 430.

Figure 4B:
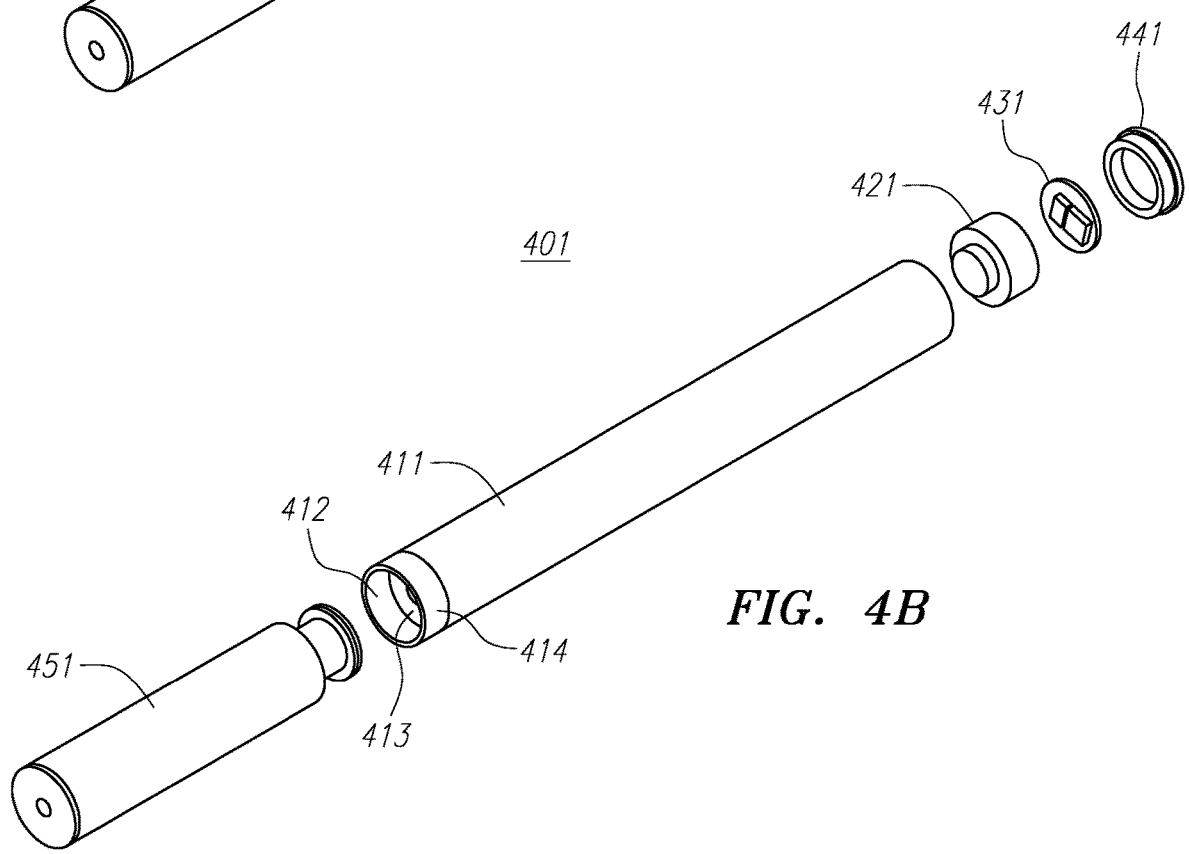
FIG. 4b shows an exploded, isometric view of an example of a rechargeable eCig that has been retrofitted according to the principles of the disclosure to form a rechargeable SCig.

FIG. 4b shows an exploded view of another embodiment of an SCig 401 that is constructed according to the principles of the disclosure. The SCig 401 comprises a conventional rechargeable eCig battery (not shown) that resides in housing 411, a cartomizer 451, and a removable/attachable data logging circuitry 431. In this embodiment, the SCig 401 can further comprise a data logging circuitry board support 421, adapted to support the data logging circuitry 431, and a cover 441. The cover 441 can comprise a lens or device to cover one end of the SCig 401. The data logging circuitry 431 can comprise the logging device 100 (shown in FIG. 1).

In the depicted embodiment, the rechargeable eCig battery in housing 411 can be retrofitted with the data logging circuitry 431 by removing the existing cover 441, if present, coupling the data logging circuitry board support 421 and the data logging circuitry 431 to the rechargeable eCig battery, and connecting the cover 441 to the rechargeable eCig battery housing 411. In the current embodiment, the charging connection 412, which comprises first and second electrical contacts 413, 414, respectively, that are in electrical contact with the positive and negative terminals (not shown) of the battery residing in the housing 411, can be configured for connection to the cartomizer 451, for connection to a charging station or device (see, for example, FIG. 13), and can also serve as a data connection to a pack, a fixture, a computer, or a different networked device. When the charging connection 412 is connected to a device that can send or receive data communications, the data logging circuitry 431 or other electronic circuit present on the SCig 401 can connect through the charging connection 412. The data logging circuitry board support 421 may include contact points and/or communication links for conveying the logging data signals and control signals between the conventional eCig 411 and data logging circuitry 431. The control signals may include sensor signals received from one or more sensors provided in the conventional eCig 411, such as, e.g., a pressure sensor (not shown), a temperature sensor (not shown), a voltage sensor (not shown), a capacitor sensor (not shown), or the like. The data logging circuitry board support 421 may include a configuration that is configured to receive the data logging circuitry 431 and hold it snuggly to minimize any forces that may be encountered, such as, e.g., dropping of the SCig 401.

In one embodiment the data logging circuitry board support 421 can already be included within the housing 411. The data logging circuitry board support 421 can comprise a pre-existing circuitry (not shown). The pre-existing circuitry can be used by the rechargeable eCig battery to determine when a user is using the eCig and/or to send visual signals to a user. In this embodiment the data logging circuitry board support 421 can be pre-existing circuitry, and the data logging circuitry 431 can be connected to the data logging circuitry board support 421. The data logging circuitry board support 421 can provide control signals to the data logging circuitry 431 In another embodiment the data logging circuitry 431 can send and receive signals by modulating data on to the charge line and responding to data modulated onto the charge line by a pack, a fixture, a computer, or a different networked device.

Figure 5:
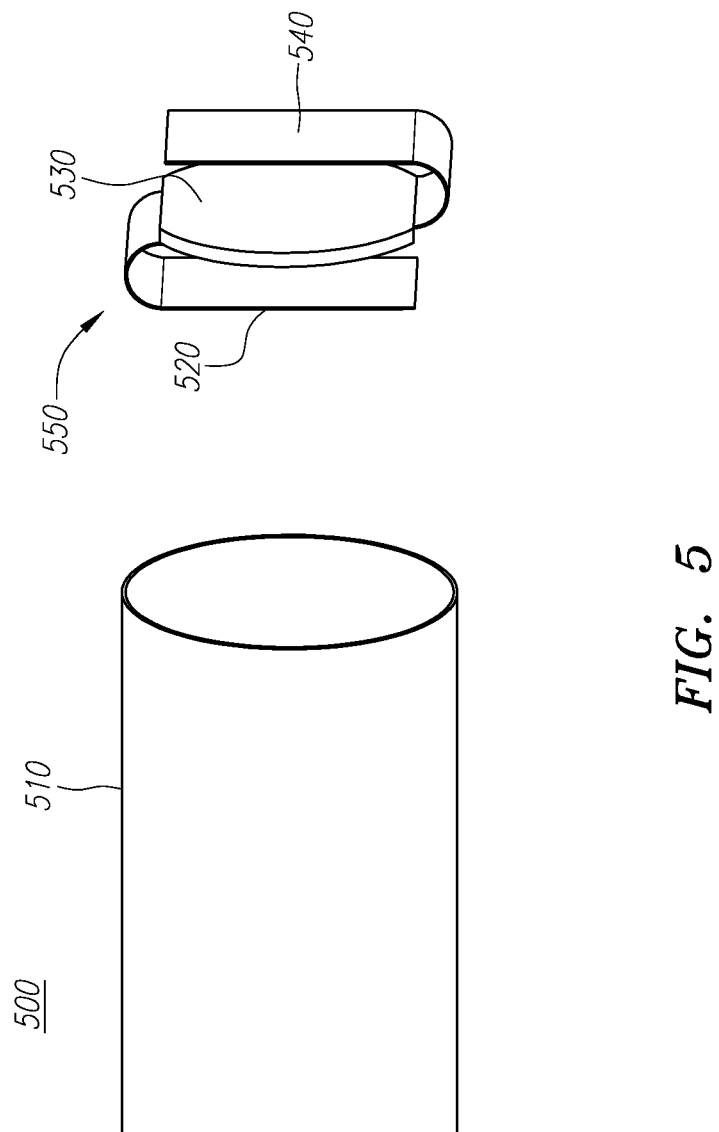
FIG. 5 shows another example of an SCig that is constructed according to the principles of the disclosure.

FIG. 5 shows an embodiment of an SCig 500 that is constructed according to the principles of the disclosure. The SCig 500 comprises a conventional eCig 510 and an attachable/insertable retrofitting unit 550. The retrofitting unit comprises a first contact portion 520 and a data logging circuitry 530. The first contact portion 520 may include communication links, including, e.g., a bus, a contact pin, a data line, or the like. The data logging circuitry 530 may include the logging device 100 (shown in FIG. 1). The data logging circuitry 530 may include an LED. The data logging circuitry 430 can comprise a transducer (not shown), such as, e.g., an LED, an infra-red diode, an antenna, or the like. The data logging device 530 can be configured to broadcast data to an external device. The LED can be utilized by the SCig 500 to send visual indications to a user. The visual indications can include whether the SCig 500 is on, and whether the SCig 500 needs recharging, among other indications. The retrofitting unit may comprise a second contact portion 540. The second contact portion 540 may include communication links. In one embodiment, the second contact portion 540 may include a transducer (not shown), such as, e.g., an LED, an infra-red diode, an antenna, or the like. The second contact portion 540 can be configured to broadcast data to an external device. The first and/or second contact portions 520, 540 may be made of a clear plastic material that may allow a light beam emitted from the data logging circuitry 530 to travel through the first and/or second contact portions 520, 540. The first contact portion 520 can comprise an interface that is separate from the interface comprising part of the second contact portion 540. In another embodiment, the first contact portion 520 and the second contact portion 540 can be integrated into a signal contact portion (not shown). In one embodiment, the retrofitting unit 550 can be removed from the SCig 500. The retrofitting unit 550 can be removed from the SCig 500 and the first contact portion 520 can be connected to a fixture or other device for downloading data thereto.

FIG. 6 shows an example of a mouthpiece 600 that may be attached to a traditional tobacco-based cigarette (not shown). The mouthpiece 600 comprises a housing 610, a retrofitting unit 620, a power source 630, and a cap 670. The housing 610 is configured to receive and securely hold a filter end of a traditional cigarette at one end of the housing 610. The housing 610 is further configured to receive and hold the retrofitting unit 620 and the power source 630 at its other end. The retrofitting unit 620 may include first and/or second contact portions 660, 650. The retrofitting unit 620 can include a data logging circuitry 640, which can include the logging device 100 (shown in FIG. 1). The retrofitting unit 620 and/or the first and/or second contact portions 660, 650 can include one or more sensors (not shown) to measure airflow, time of day, puff frequency, puff duration, puff strength, puff volume, temperature of smoke, temperature of the cigarette filter, pressure, nicotine payload delivered to user, gas and particulate phase component delivery to user, and the like. The cap 670 encloses the retrofitting unit 620 within the housing 610.

Figure 7A:
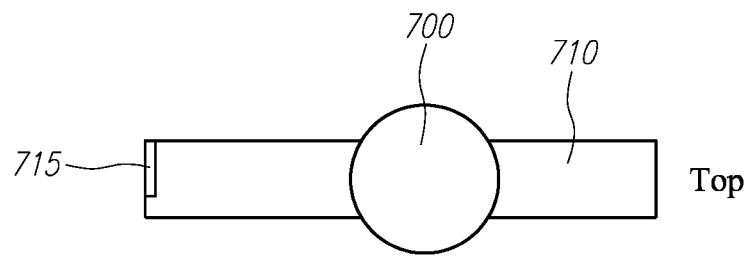
FIG. 7A shows a top view of an example of a retrofitting unit that is constructed according to the principles of the disclosure.

FIG. 7A shows a top view of an example of a retrofitting unit that is constructed according to the principles of the disclosure. The retrofitting unit comprises a logging device 700, a first contact portion with contacts 710 and a second contact portion with contacts 715. The logging device 700 may be substantially the same as the logging device 100, shown in FIG. 1.

Figure 7B:
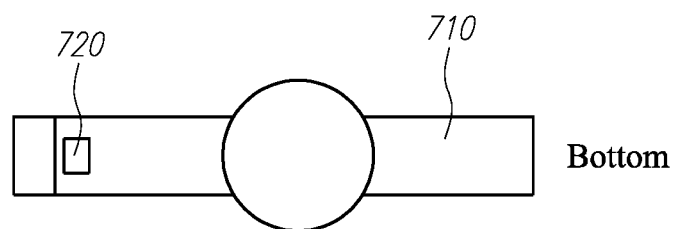
FIG. 7B shows a bottom view of the retrofitting unit of FIG. 7A.

FIG. 7B shows a bottom view of the retrofitting unit of FIG. 7A. As seen, the retrofitting unit may include an LED 720. In various embodiments the LED 720 can be placed on the logging the device, the first contact portion with contacts 710, and/or the second contact portion with contacts 715.

Figure 8A:
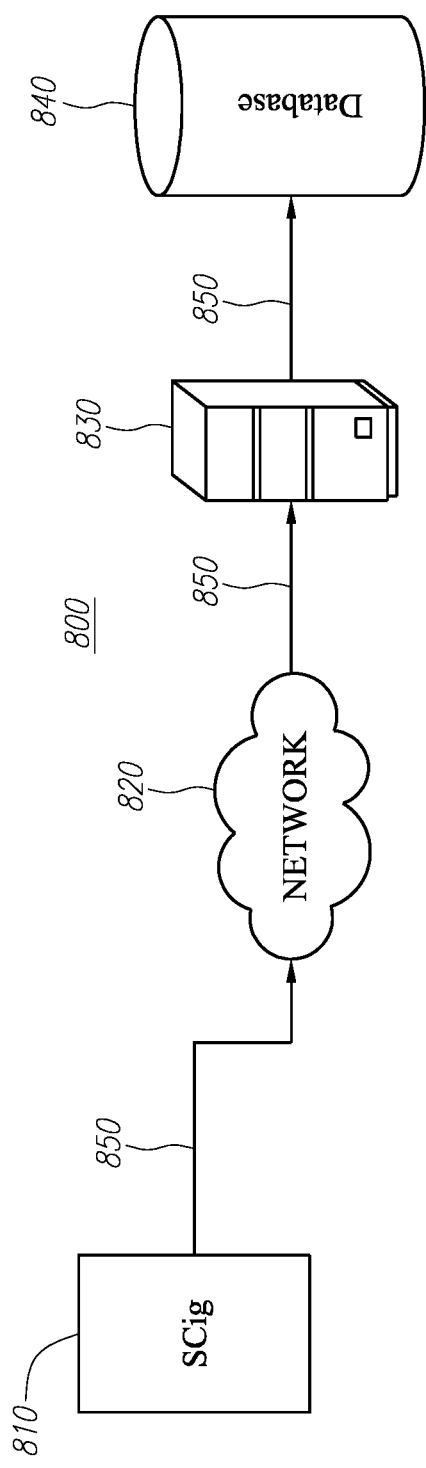
FIGS. 8a and 8b show examples of a system for monitoring, storing, and processing logging data, according to the principles of the disclosure.

FIG. 8a shows an embodiment of the disclosure comprising a system 800 for monitoring, storing, and processing logging data, according to the principles of the disclosure. The system 800 comprises an SCig 810 (or a traditional cigarette retrofitted with a retrofitting unit as seen in FIG. 6, or a conventional eCig retrofitted with a retrofitting unit as seen in FIG. 4b) that may communicate with a server (or computer) 830, via a network 820, over a communication link 850. The server 830 may store logging data in a database 840 for an individual user and/or each SCig 810. The database 840 may be provided locally (e.g., inside the server or near the server), or remotely. The database 840 may include a unique record for each SCig 810 and/or individual user. Each record may include various fields for the different types of data associated with the SCig log data and/or the user activity log data. The logging data may be accessed and retrieved from the database 840 and processed to generate reports that may be configured to provide historical data about an individual user's and/or SCigs' smoking activities.

Figure 8B:
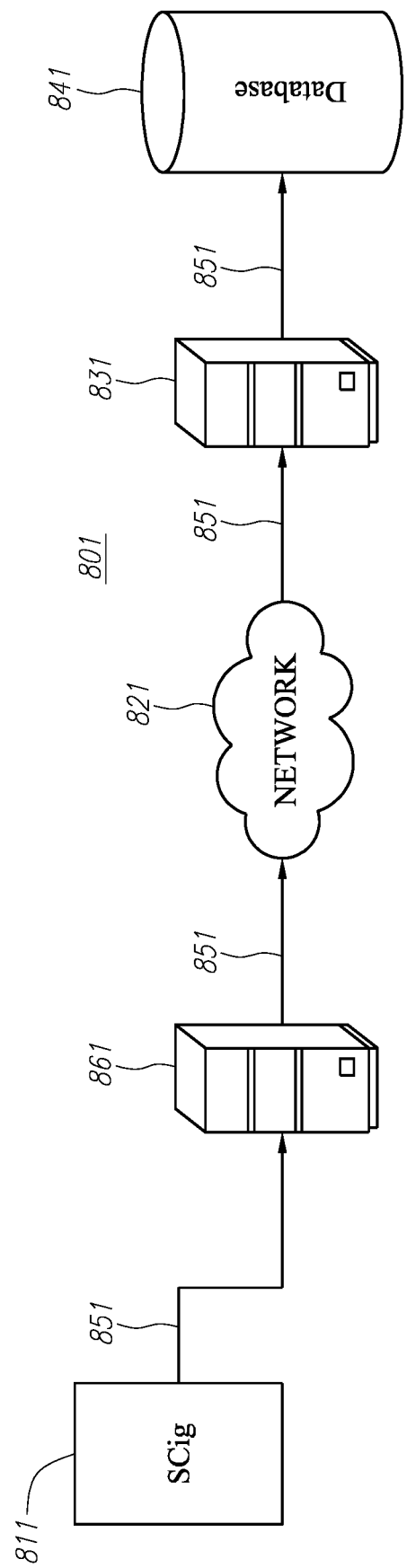

FIG. 8b illustrates another embodiment of the disclosure comprising a system 801 for monitoring, storing, and processing logging data, according to the principles of the disclosure. The system 801 comprises an SCig 811 (or a traditional cigarette retrofitted with a retrofitting unit as seen in FIG. 6, or a conventional eCig retrofitted with a retrofitting unit as seen in FIG. 4b) that may communicate with a first server (or first computer, first mobile phone, first personal digital assistant, etc.) 861, over a communication link 851. The first server 861 can communicate with a network 821 over a communication link 851. The network 821 can then communicate with a second server (or second computer) 831. The second server 831 can store logging data in a database 841 for an individual user and/or each SCig 811. The database 841 may be provided locally (e.g., inside, or near, one of the servers 861, 831), or remotely. The database 841 may include a unique record for each SCig 811 and/or individual user. Each unique record may include various separate logs for the different types of data associated with an individual SCig log data and/or an individual user activity log data. The logging data may be accessed and retrieved, either locally or remotely, from the database 841 and processed to generate reports that can be configured to provide historical data about an individual user's and/or an individual SCig's smoking activities.

Figures 9A, 9B:
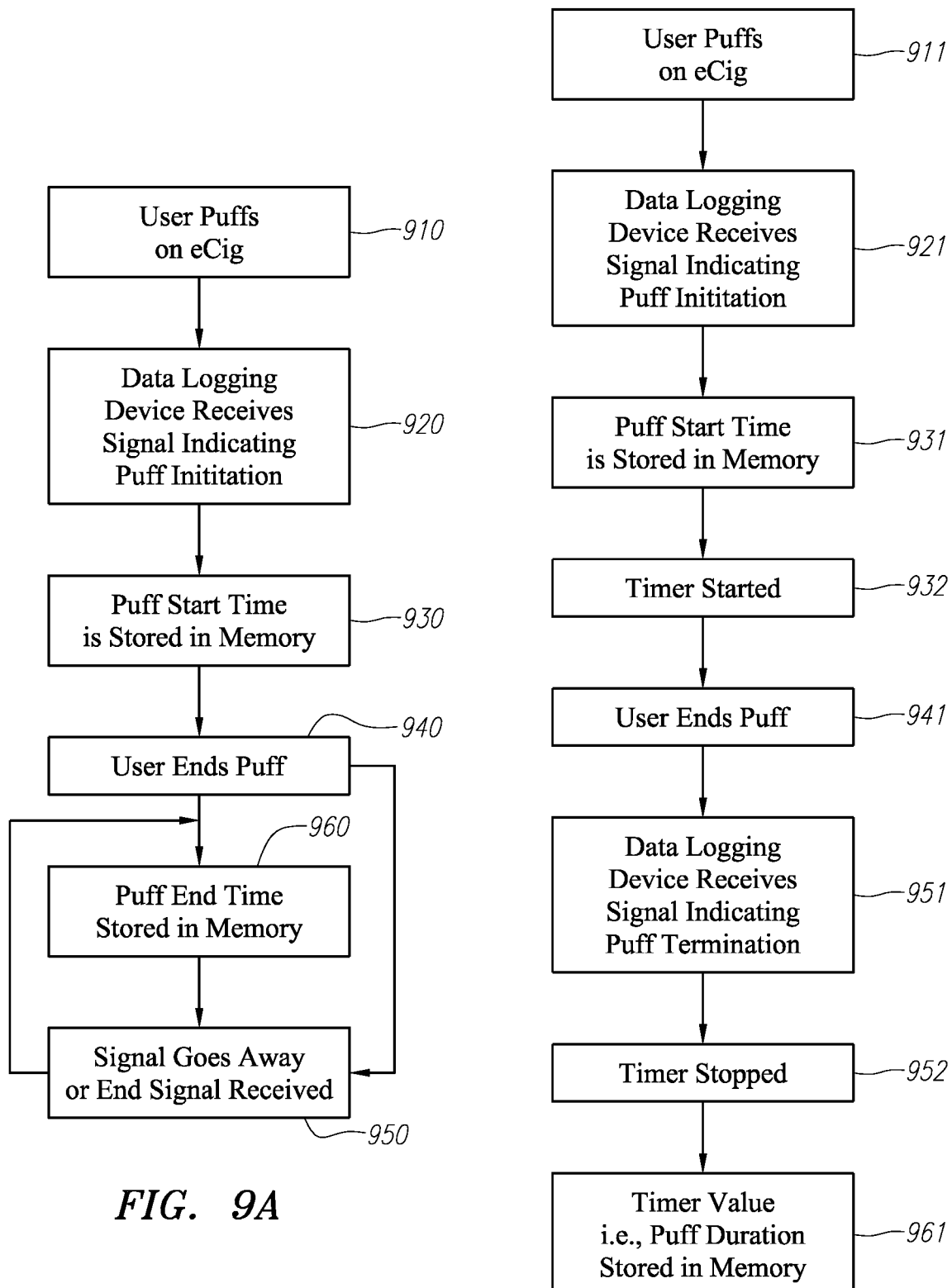
FIGS. 9A and 9B are flowcharts illustrating exemplary methods of recording puff durations or other data.

FIG. 9a illustrates a flowchart showing a method for logging data as used by one embodiment of the disclosure. The method comprises the following steps:

At step 910, a user taking a puff on one of an SCig, on a traditional cigarette that has been retrofitted with a retrofitting unit as seen in FIG. 6, or on a conventional eCig that has been retrofitted with a retrofitting unit as seen in FIG. 4b;

At step 920, a data logging device receives a signal indicating that a puff has been initiated. The signal can include the output of a transistor, an I/O line of a processor or application-specific integrated circuit (ASIC), or the output signal of a sensor;

At step 930, the data logging device stores the puff start time in memory. The memory can be part of the data logging device or can be operably connected to the data logging device such that the data logging device can transmit information to the memory;

At step 940, the user ends the puff;

At step 950, the signal stops being sent or an end signal is received; and

At step 960, the data logging device stores the puff end time in memory.

FIG. 9b illustrates a flowchart showing a method for logging data as used by another embodiment of the disclosure. The method comprises the following steps:

At step 911, a user takes a puff on one of an SCig, on a traditional cigarette that has been retrofitted with a retrofitting unit as seen in FIG. 6, or on a conventional eCig that has been retrofitted with a retrofitting unit as seen in FIG. 4b;

At step 921, a data logging device receives a signal indicating that a puff has been initiated. The signal can include the output of a transistor, an I/O line of a processor or ASIC, or the output signal of a sensor;

At step 931, the data logging device stores the puff start time in memory. The memory can be part of the data logging device or can be operably connected to the data logging device such that the data logging device can transmit information to the memory;

At step 932, a timer is started. The timer can be operably coupled to the data logging device or can be integral to the data logging device;

At step 941, the user ends the puff;

At step 951, the data logging device receives a signal indicating that the puff has been terminated or the signal indicating activation terminates;

At step 952, the timer stops; and at step 961, a value of the timer, or the duration of the puff, is stored in memory.

While FIG. 9A and FIG. 9B describe a method of determining and storing puff duration or the time of each puff, other information could instead be logged by the data logging device with the method. The other data that could be logged using the methods in FIGS. 9A and 9B include puff frequency, puff strength, puff volume, temperature of smoke, temperature of a cigarette filter if present, pressure, nicotine payload delivered to the user, gas and particulate phase component delivery to the user, and the like. In one embodiment, the data logging device can increment a puff count value after each puff is recorded. In various embodiments the puff count value can track the number of puffs that have been taken on a particular battery or device since the device has been manufactured, the number of puffs that have been taken on a particular battery since the last recharging, the number of puffs that have been taken since a new cartomizer has been connected to the battery, or the number of puffs that have occurred since other events have taken place. In yet other embodiments, the total duration of time that puffs have been taken can be tracked, recorded, and used by the data logging device In embodiments of the disclosure, a data logging device may transfer data via a uni-directional or a bi-directional communication link.

Figure 10A:
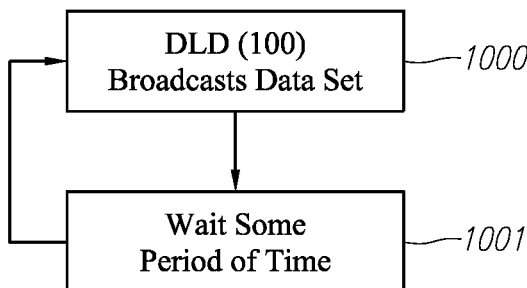
FIGS. 10A, 10B, and 10C are flowcharts illustrating exemplary methods of transmitting data sets from data logging devices.

FIG. 10A illustrates one embodiment of a method for a uni-directional data transfer by a data logging device comprising the following steps:

At step 1000, a data logging device (such as 100 in FIG. 1) broadcasts a data set.

At step 1001, the data logging device then waits a predetermined period of time and then returns to step 1000 and broadcasts the data set again. This method proceeds as long as the data logging device is powered or otherwise able to transmit. The data logging device can also periodically update the data set that is being broadcast.

Several different methods are available for the data logging device to be able to broadcast a data set and then rebroadcast the data set after a certain period of time. In one embodiment a signal is sent to a timer when the data logging device broadcasts a data set. The timer then counts a certain length of time and sends a signal to the data logging device to re-broadcast the data set. Alternatively, a timer can be operably coupled or integrated into the data logging device and periodically cause the data logging device to re-broadcast the data set.

Figure 10B:
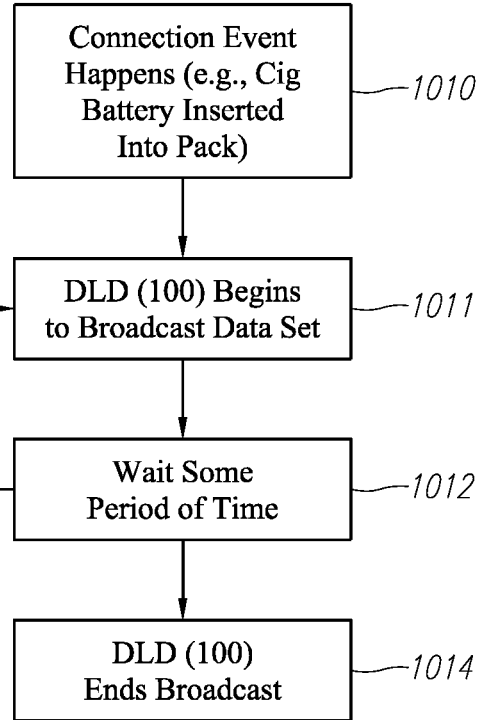

FIG. 10B illustrates another embodiment of a method for a uni-directional data transfer by a data logging device comprising the following steps:

At step 1010, a connection event occurs. The connection event can comprise an SCig battery inserted into a pack or other charging device, an SCig connected to a data analyzer or the like, a retrofitting unit connecting to a data analyzer or the like, or other events that would be apparent to a person having ordinary skill in the art.

At step 1011, the data logging device (such as the embodiment 100 shown in FIG. 1) then begins to broadcast a data set.

At step 1012, the data logging device then waits a period of time and repeats, at step 1013, a broadcast of the data set a selected number of times. When repeating a broadcast of the data set, the number of repeat broadcasts can be limited to a certain number of rebroadcasts or to until a certain amount of time has passed after the connection even has occurred.

At step 1014, the data logging device can then stop broadcasting the data set once a programmed number of broadcasts has occurred or once a specified period of time has passed.

Figure 10C:
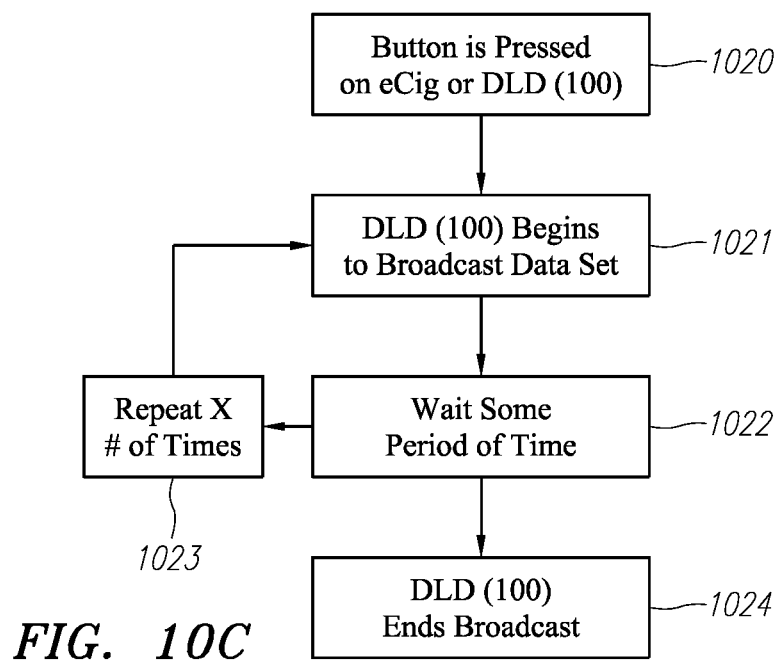

FIG. 10C illustrates yet another embodiment of a method for a uni-directional data transfer by a data logging device, the method comprising the following steps:

At step 1020, a button is pressed on an SCig, retrofitting unit, or a data logging device.

At step 1021, the data logging device (such as the embodiment 100 shown in FIG. 1) then begins to broadcast a data set.

At step 1022, the data logging device then waits a period of time and repeats, at step 1023, a broadcast of the data set. When repeating a broadcast of the data set, the number of repeat broadcasts can be limited to a certain number of rebroadcasts or to until a certain amount of time has passed after the connection even has occurred.

At step 1024, the data logging device can then stop broadcasting the data set once a programmed number of broadcasts has occurred or once a specified period of time has passed.

Figure 11:
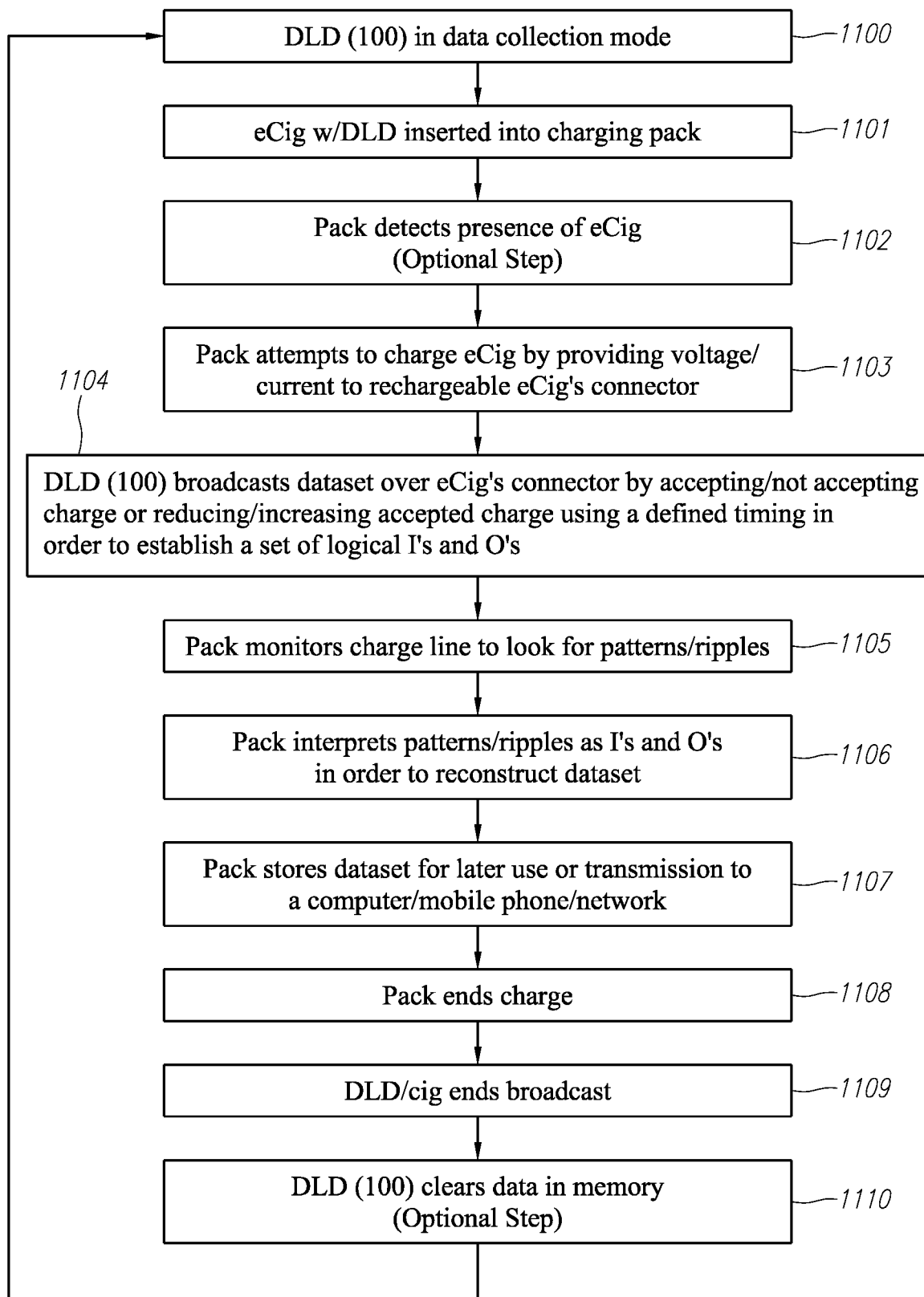
FIG. 11 is a flowchart illustrating an exemplary method of broadcasting a data set stored in a data logging device.

FIG. 11 illustrates another embodiment of a method for uni-directional data transfer by a data logging device comprising the following steps:

At step 1100, the data logging device (such as the embodiment 100 shown in FIG. 1) collects data from an SCig, a retrofitting unit, or the like while in a data collection mode.

At step 1101, a product comprising a rechargeable battery and the data logging device operably attached thereto is then electrically or otherwise coupled to a charging device. In one embodiment (not represented in FIG. 11), the rechargeable battery with the data logging device operably attached thereto is physically separated from (e.g., unscrewed from) the other components of the SCig or the retrofitted eCig before the rechargeable battery and the data logging device are electrically or otherwise coupled to the charging device. The charging device can comprise a charging pack, a USB connector, or other type of charger.

At step 1102, the charging device can optionally detect the presence of the product comprising a data logging device.

At step 1103, the charging device then attempts to charge the product by providing a voltage to the product over a connector or other device.

At step 1104, the data logging device broadcasts a data set over the connector of the product by varying the accepted current or voltage using a defined timing in order to establish a set of logical signals. The data logging device can vary the accepted current or voltage through various means, including accepting or not accepting current or voltage, and by reducing or increasing the accepted current or voltage. The logical signals can comprise sets of 1s and 0s.

At step 1105, the charging device monitors the charge line to look for patterns or ripples that comprise the logical signals.

At step 1106, the charging device interprets the patterns or ripples, e.g. as 1s and 0s, to reconstruct the data set being broadcast by the data logging device.

At step 1107, the charging device stores the data set for use by, or transmission to, a computer, mobile phone, network, or the like. The transmission from the charging device can occur concurrently with the transfer of the data set from the data logging device to the charging device, or can be stored internally for a later use or transmission.

At step 1108, the charging device ceases charging the product; and, at step 1109, the data logging device ceases broadcasting.

Optionally, at step 1110, the data logging device can clear the data set that is stored in memory on the data logging device once the charging device has ceased charging the product. The data logging device can also be programmed so that the data is only cleared once the charging device has ceased charging the product and the rechargeable battery is charged to a certain threshold level.

The data logging device then returns to step 1100 and re-enters data collection mode.

While the methods shown and described in FIGS. 10A, 10B, 10C, and 11 are utilizing unidirectional data links, bi-directional data links could also be employed.

According to a further aspect of the disclosure, a computer program is provided on a computer-readable medium that, when executed on a computer (e.g., microcontroller 110 and/or server 830) may cause each of the processes described herein to be carried out. The computer-readable medium may include a code section or code segment for each step of the processes described herein.

Figure 12:
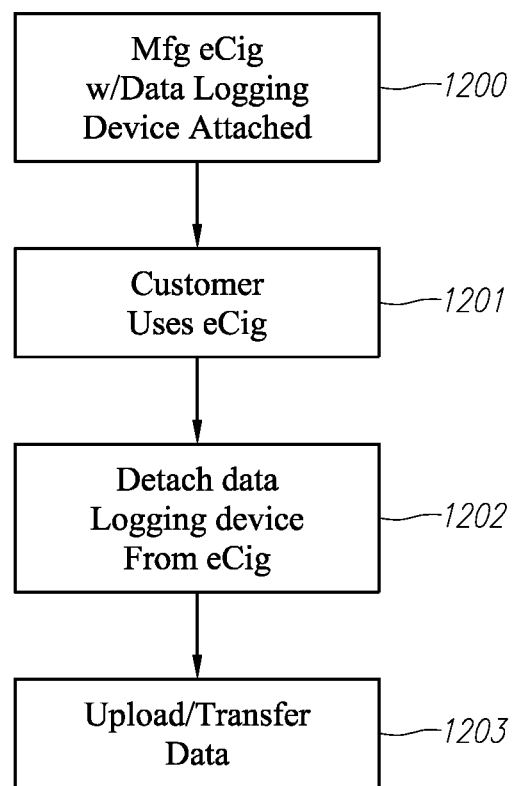
FIG. 12 is a flowchart illustrating an exemplary method of producing and acquiring data from an eCig.

FIG. 12 illustrates a method of producing and acquiring data from an eCig comprising the following steps.

At step 1200, an eCig is manufactured with a data logging device attached thereto. The data logging device can be integral to the eCig or can be removable from the eCig while still allowing the eCig to function.

As represented by step 1201, a customer can then use the eCig as they normally would.

At step 1202, the customer can then detach the data logging device from the eCig. The factor that determines when the data logging device is detached from the eCig can be one or more of a variety of factors. These factors can include a specific length of time since the eCig was manufactured, a specific length of time since the eCig was first used, the cumulative number of puffs that have been made on the eCig, a duration of time that the eCig has been puffed on, a duration of time the heater in the eCig has been activated, when the eCig battery drops below a voltage threshold, or other factors that are appropriate.

At step 1203, data on the data logging device can then be uploaded or transferred. The data can be transferred to a computer, a server, or other electronic storage medium that can store the data and/or transfer the data to a predetermined location.

Figure 13:
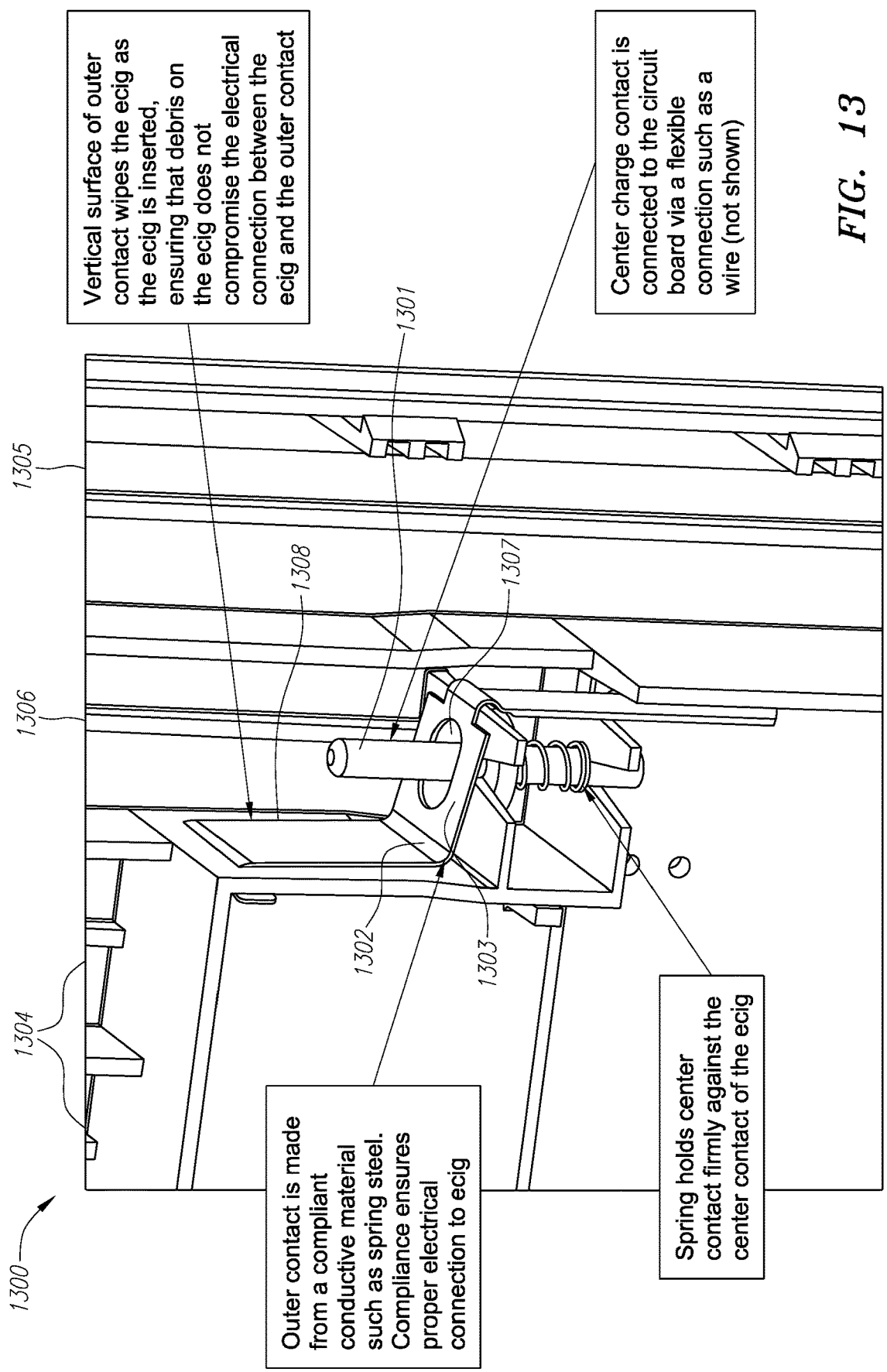
FIG. 13 is a fragmentary, isometric view of an exemplary charging system with its cover removed.

FIG. 13 illustrates an example of a charging system within a charging holder (pack) 1300. Within the charging holder 1300, there are several slots for a full eCig, or components of an eCig (e.g., an eCig cartridge or an eCig body, the eCig body comprising, for example an eCig housing and an eCig battery with or without an attached data logging device or other electronics). In this example, an eCig cartridge can be placed in one or more of the slots 1304, the full eCig can be placed in one or more of the slots 1305, and the eCig body can be placed in one or more of the slots 1306. When the eCig body is placed in one of the slots 1306, the battery of the eCig can be charged.

In order to charge an eCig battery using a charging system (e.g., a pack, docking station, or some other modality), a reliable electrical connection must be established between the battery and the charging system. A commonly used method of establishing this reliable electrical connection is to screw the charging connection (e.g., 412 depicted in FIG. 4*b*) of the eCig battery housing (e.g., 411 depicted in FIG. 4*b*) into the charging system. However, a more convenient way to make the electrical connection is by using a push-in style of contact, which also has the benefit of not requiring the user do anything more than simply pushing the eCig battery housing into the charging system.

In the embodiment depicted in FIG. 13, this push-in style of contact includes a center contact 1301 to provide one polarity of the charge signal and an outer contact 1302 to provide the other polarity. The center contact 1301 can be a spring or a pin or a spring-loaded pin, as illustrated in FIG. 13. In the embodiment depicted in FIG. 13, the spring presses the charging system's center contact 1301 firmly against the first electrical contact 413 (see FIG. 4*b*) of the eCig battery housing (see 411 in FIG. 4*b*), thereby establishing an electrical connection between one pole of the battery and one pole of the charging system, while ensuring that electrical continuity is maintained, even if the system is jostled. The outer contact 1302 of the charging system depicted in FIG. 13 can be made from a compliant conductive material, such as conductively plated spring steel. When the rechargeable battery housing 411 is installed into the charging system, the second electrical contact 414 (see FIG. 4*b*) rests against a top surface 1303 of the outer contact 1302, which includes a hole 1307 through which the center contact 1301 projects. The outer contact 1302 is shaped so as to flex when the eCig battery housing is pushed into place in the charging system. The compliance of the outer contact 1302 ensures a reliable electrical connection to the eCig battery, even during jostling, and accommodates for variations in the mechanical dimensions of the eCig battery and charging system.

Sometimes, debris or deposits can accumulate on the outer contact 1302 of the eCig battery. Alternatively, debris or deposits can accumulate on the first and second electrical contacts (see 413 and 414, respectively, in FIG. 4*b*). Such debris or deposits can inhibit the electrical connection between the eCig battery and the charging system. To address this problem, the outer contact 1302 can be configured to "self-clean." For example, the vertical surface 1308 of the outer contact 1302 can be configured to scrape debris off the first and second electrical contacts 413, 414 as the eCig battery housing 411 is pushed into the charging system, thereby removing any debris buildup at the sites of electrical connection.

Figure 14:
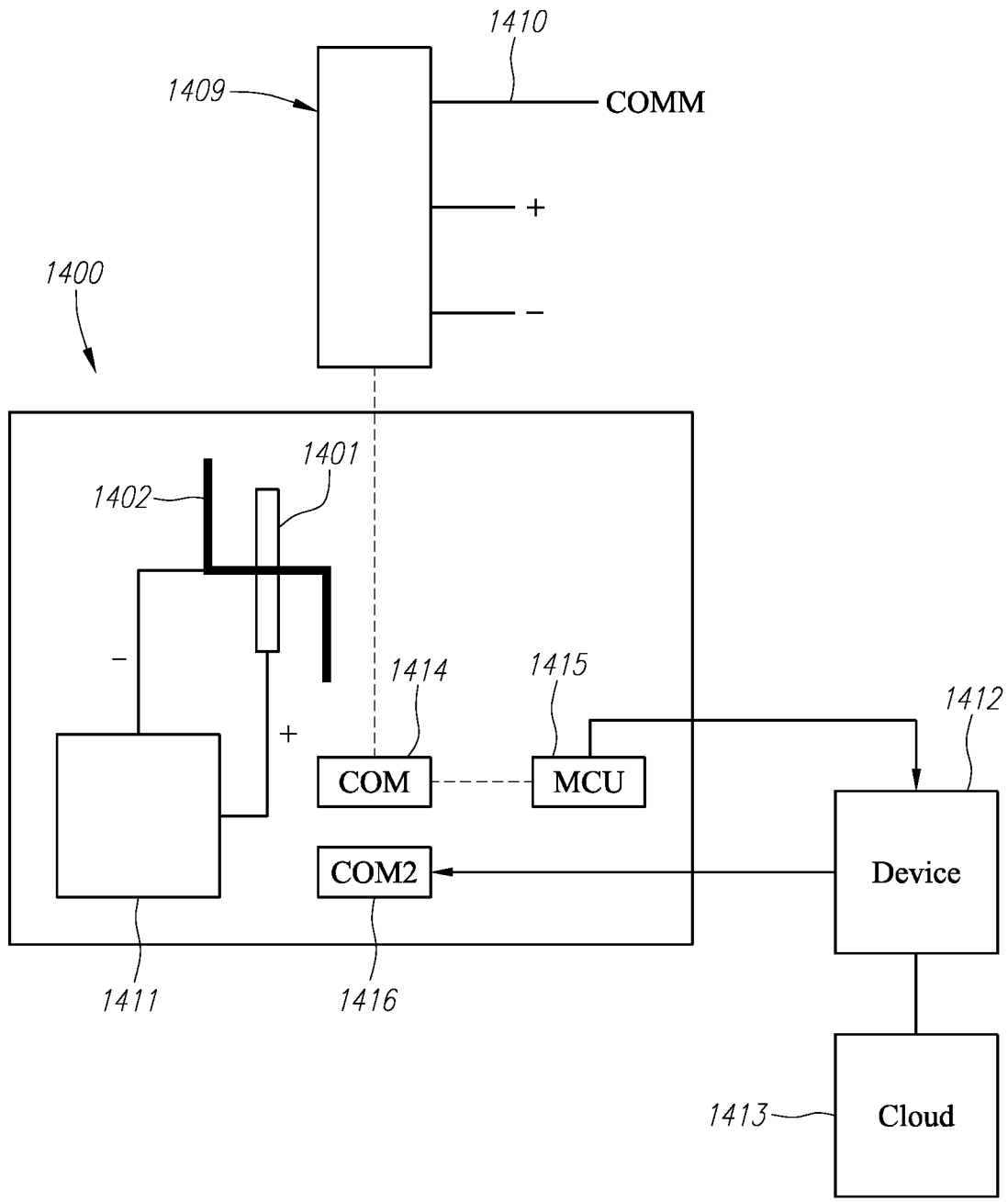
FIG. 14 is a diagram of an exemplary charging system capable of receiving and transmitting data.

FIG. 14 illustrates an embodiment of a charging system within a charging holder (pack) 1400. The illustrated charging holder differs from that shown in FIG. 13 in that it includes a dedicated communication pathway for data to be transferred from an eCig 1409 to an electronic memory 1414 within the charging holder 1400. The charging holder 1400 comprises a first contact 1401 to provide one polarity of the charge signal and a second contact 1402 to provide the other polarity. The first contact 1401 and the second contact 1402 can be connected to a pack battery 1411 to recharge the eCig 1409. The charging holder 1400 can also include a third contact or a plurality of contacts that can connect to a third contact 1410 or plurality of contacts on the eCig 1409. The third contact can allow for data transfer to occur to the electronic memory 1414.

The electronic memory 1414 can be operably coupled to a microcontroller 1415 which can communicate with a device 1412 to transfer any data stored within the charging holder 1400 to the device 1412. Once the data is stored within the device 1412, it can then be transferred to a separate location, a group of computer servers, or to the cloud 1413. The device 1412 can also communicate with a second electronic memory 1416. While communicating with the second electronic memory 1416, the device 1412 can upload new software, drivers, instructions, or other desired information to be used in the operation and function of the charging holder 1400. The charging holder 1400 is configured to transmit and/or receive (transceive) logging data signals and control signals from/to the eCig 1409 and/or device 1412. In one embodiment, the electronic memory 1414, the microcontroller 1415, and the second electronic memory 1416 may be integrated into a single part.

In some embodiments it is necessary to unscrew, pull, or otherwise take the eCig apart to put the rechargeable portion of the eCig into the charging holder. In this embodiment the data logging device is included within the rechargeable portion of the eCig. Having the data logging device within this portion allows for a less expensive product as the data logging device can be re-used as the rechargeable portion can be used with multiple disposable cartomizers or cartridges.

In some embodiments, using the pack as a storage and transmitter of data acquired by the data logging device can have several important advantages. The charging holder has a larger battery than the rechargeable portion of the eCig and as a result has more power to upload data to a computer, server, or other device. The charging holder can also include multiple communication options (i.e., Bluetooth, LTE, wireless, etc.). The charging holder can also comprise an increased processing power and/or a larger amount of memory within the pack. By having the data automatically download to the pack when the rechargeable portion of the eCig is placed within the pack and having the pack automatically transfer the data to a computer or other device either when a certain event occurs (e.g., when the charging holder is plugged into a computer to charge or wirelessly connected through a Bluetooth or other broadcasting device) the user is not required to do anything different from their normal method of using the eCig and pack.

Figure 15:
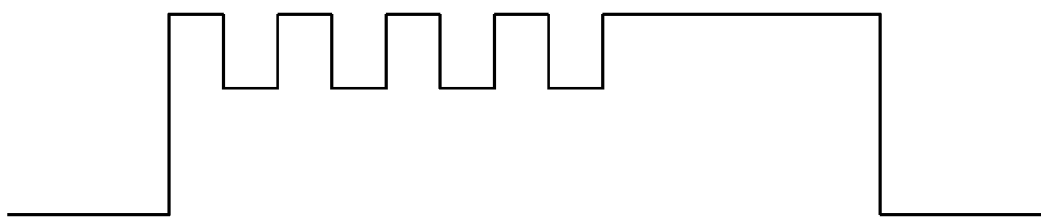
FIG. 15 is a diagram of a high and low current flow for data transmission.

In alternative embodiments, a signal can be sent to an electronic medium within a charging holder through a broadcasting signal sent by an eCig during the recharging process. One example of such a broadcasting signal is illustrated in FIG. 15. This broadcast is sent through the electrical circuit that is used to recharge the eCig and can be of any variety that allows the data to be transferred. In the illustrated embodiment two levels of current, a peak level and a low level, are illustrated. The charging holder can be configured to detect the level of current flowing through the system at any point in time and is able to identify the information being transmitted by the eCig through this current flow. The duration of time a peak level and a low level of current are present within the circuit can communicate to the charging holder a specific set of information. In such an embodiment, the charging pack does not need to include a communication interface for connection to the eCig.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a super computer, a personal computer, a laptop computer, a palmtop computer, a notebook computer, a desktop computer, a workstation computer, a server, or the like, or an array of processors, microprocessors, central processing units, general purpose computers, super computers, personal computers, laptop computers, palmtop computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communication link," as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The wired medium may include a power supply line. The RF communication link may include, for example, WiFi, WiMAX, IEEE 802.11, DECT, 0G, 1G, 2G, 3G or 4G cellular standards, Bluetooth, Bluetooth Smart, Bluetooth Low Energy, and the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, or the like, or any combination of the foregoing, any of which may be configured to communicate data via a wireless and/or a wired communication medium. These networks may run a variety of protocols not limited to TCP/IP, IRC or HTTP.

A "computer-readable medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, Bluetooth Smart, Bluetooth Low Energy, or the like.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

What is claimed:

1. A method of logging smoking data, the method comprising:
    sending a first signal indicating that a puff has been initiated on an electronic cigarette;
    receiving the first signal that a puff has been initiated by a data logging device;
    storing a first time incident in a memory by the data logging device;
    sending a second signal indicating that the puff has stopped;
    storing a second time incident in the memory by the data logging device; and
    determining a puff duration using the first time incident and the second time incident,
    storing a puff count value in the memory, wherein the puff count value tracks the number of puffs that have been taken on the electronic cigarette, wherein the puff count value tracks the number of puffs that have been taken and the total duration of time of the puff that have been taken on a particular electronic cigarette battery since the last recharging;
    storing an SCig log data in the memory, wherein the SCig log data comprises a number of times the electronic cigarette battery has been recharged.

2. The method according to claim 1, wherein the puff count value tracks the number of puffs that have been taken on the electronic cigarette since the electronic cigarette has been manufactured.

3. The method according to claim 1, wherein the puff count value tracks the number of puffs that have been taken since a new cartomizer has been connected to the battery.

4. The method according to claim 1, wherein the electronic cigarette comprises a cartomizer.

5. The method according to claim 1, further comprising incrementing a puff count value in the memory after the puff has stopped.

6. The method according to claim 1, further comprising tracking and storing a total duration of time that puffs have been taken.

7. The method according to claim 1, further comprising the step of transmitting stored smoking data.

8. The method according to claim 7, wherein the step of transmitting stored smoking data comprises:
    broadcasting a data set comprising smoking data stored by the data logging device; waiting a predetermined period of time; rebroadcasting the data set a predetermined number of times; and ending broadcasting of the data set.

9. An electronic cigarette comprising:
    a sensor configured to send a first signal indicating that a puff has been initiated and send a second signal indicating that the puff has stopped;
    a data logging device configured to receive the first signal that a puff has been initiated, store a first time incident in a memory, receive the second signal that a puff has been stopped, store a second time incident in the memory, determine a puff duration using the first time incident and the second time incident, and store a puff count value in the memory, wherein the puff count value tracks the number of puffs that have been taken on the electronic cigarette, wherein the puff count value tracks the number of puffs that have been taken and the total duration of time of the puff that have been taken on a particular electronic cigarette battery since the last recharging, and wherein the data logging device is configured to store a number of times the electronic cigarette battery has been recharged.

10. The electronic cigarette according to claim 9, further comprising a housing wherein the data logging device is disposed within the housing, the data logging device comprising a microcontroller, the memory, and a data interface, wherein the data logging device is configured to detect, monitor, and log smoking activity data.

11. The electronic cigarette according to claim 9, further comprising:
    a housing;
    a power supply located within the housing;
    an atomizer electrically coupled to the power supply; and
    a liquid solution fluidly coupled to the atomizer.

12. The electronic cigarette according to claim 9, wherein the data logging device further comprises a clock.

13. The electronic cigarette according to claim 9, wherein the data logging device further comprises a timer.

14. The electronic cigarette according to claim 9, wherein the data logging device further comprises at least one data logging sensor.

15. The electronic cigarette according to claim 9, wherein the data logging device is further configured to log a smoking activity data on the memory.

16. The electronic cigarette according to claim 9, wherein the data logging device is further configured to transmit a stored smoking activity data.

17. The electronic cigarette according to claim 16, wherein the data logging device is further configured to transmit the stored smoking data wirelessly.

18. The electronic cigarette according to claim 16, wherein the data logging device is further configured to broadcast a data set comprising smoking data stored by the data logging device, wait a predetermined period of time, rebroadcast the data set a predetermined number of times, and end broadcasting of the data set.

19. The electronic cigarette according to claim 9, wherein the puff count value tracks the number of puffs that have been taken on a particular electronic cigarette battery since the device has been manufactured, the number of puffs that have been taken on a particular electronic cigarette battery since the last recharging, and the number of puffs that have been taken since a new cartomizer has been connected to the electronic cigarette battery.

\* \* \* \* \*